United States Patent
Valtzer (10) Patent No.: US 10,779,888 B2
(45) Date of Patent: Sep. 22, 2020

(54) SMOKE DISSIPATION ADAPTER FOR LASER HANDPIECES

(71) Applicant: LUMENIS LTD., Yokneam (IL)

(72) Inventor: Emri Valtzer, Haifa (IL)

(73) Assignee: LUMENIS LTD., Yokneam (IL)

( * ) Notice: Subject to any disclaimer, the term of this patent is extended or adjusted under 35 U.S.C. 154(b) by 252 days.

(21) Appl. No.: 15/918,168

(22) Filed: Mar. 12, 2018

(65) Prior Publication Data
US 2018/0263696 A1    Sep. 20, 2018

Related U.S. Application Data

(60) Provisional application No. 62/471,529, filed on Mar. 15, 2017.

(51) Int. Cl.
*A61B 18/20* (2006.01)
*A61M 35/00* (2006.01)
*A61B 18/00* (2006.01)

(52) U.S. Cl.
CPC ......... *A61B 18/203* (2013.01); *A61M 35/003* (2013.01); *A61B 2018/0047* (2013.01); *A61B 2018/00476* (2013.01); *A61B 2018/00577* (2013.01); *A61B 2018/00625* (2013.01); *A61B 2018/202* (2013.01); *A61B 2218/006* (2013.01); *A61B 2218/008* (2013.01); *A61M 2202/02* (2013.01); *A61M 2205/051* (2013.01); *A61M 2210/04* (2013.01)

(58) Field of Classification Search
CPC ........ A61B 18/203; A61B 2018/00577; A61B 2018/00476; A61B 2018/00625; A61B 2218/006; A61B 2218/008; A61B 2018/0047; A61B 2018/051; A61B 2018/202; A61M 35/003; A61M 2202/02; A61M 2205/051; A61M 2210/04
USPC .................. 55/385.1; 604/114; 606/2, 9, 41; 607/89, 101; 600/8, 632
See application file for complete search history.

(56) References Cited

U.S. PATENT DOCUMENTS

| | | | |
|---|---|---|---|
| 6,162,218 | A | 12/2000 | Elbrecht et al. |
| 6,264,649 | B1 | 7/2001 | Whitcroft et al. |
| 8,641,488 | B1 | 2/2014 | Shvetsov et al. |

(Continued)

FOREIGN PATENT DOCUMENTS

DE    10307260    8/2003

OTHER PUBLICATIONS

Search Report—Corresponding European Application No. 18161636, dated Feb. 6, 2019, 15 pages.

(Continued)

*Primary Examiner* — Minh Chau T Pham
(74) *Attorney, Agent, or Firm* — Isus Intellectual Property PLL; Anthony Jason Mirabito (57) ABSTRACT

An adapter for attachment to a medical application device includes an energy generating device and a distal tip for applying the energy generated to skin tissue. The adapter includes a substantially hollow body with a distal end portion and a proximal end portion. The proximal end portion is sized to mount on the distal tip of the energy generating device; the distal end portion is substantially open. The adapter further includes at least one through port extending from the proximal end portion to the open distal end portion of the adapter.

11 Claims, 8 Drawing Sheets

(56) References Cited

U.S. PATENT DOCUMENTS

| | | | |
|---|---|---|---|
| 2005/0251117 A1* | 11/2005 | Anderson | A61B 5/445 |
| | | | 606/9 |
| 2006/0189964 A1 | 8/2006 | Anderson et al. | |
| 2006/0259102 A1 | 11/2006 | Slatkine | |
| 2007/0179482 A1* | 8/2007 | Anderson | A61B 18/203 |
| | | | 606/9 |
| 2007/0255355 A1 | 11/2007 | Atlshuler et al. | |
| 2012/0203223 A1 | 8/2012 | Terry et al. | |
| 2014/0343574 A1 | 11/2014 | Ignon et al. | |
| 2015/0080879 A1* | 3/2015 | Trees | A61B 18/1445 |
| | | | 606/40 |
| 2016/0038183 A1* | 2/2016 | Ignon | A61B 17/545 |
| | | | 606/3 |
| 2018/0303515 A1* | 10/2018 | Shadduck | A61N 1/18 |
| 2019/0133642 A1* | 5/2019 | Ignon | A61B 17/54 |
| 2020/0022569 A1* | 1/2020 | Wake | A61B 1/015 |

OTHER PUBLICATIONS

Search Report—Corresponding European Application No. 18161636, dated Jun. 12, 2018, 15 pages.

* cited by examiner

SMOKE DISSIPATION ADAPTER FOR LASER HANDPIECES

RELATED APPLICATIONS

This application is related to and claims priority to U.S. Provisional Application Ser. No. 62/471,529, filed Mar. 15, 2017, the entirety of which application is herein incorporated by reference.

FIELD OF THE INVENTION

A known procedure in the medical aesthetic art is the removal of unwanted hair growth from the skin tissue through the use of a laser device. Since the laser device essentially burns and vaporizes the hair shafts, it is a common occurrence that the hair, upon being vaporized, may produce smoke (known as a "plume") and noxious odors.

A recent study published in the JAMA dermatology journal in July 2016 by Dr. Gary Chuang and his colleagues at Mass General Hospital studied the gaseous and particular content of laser hair removal plume. (Chuang G S, Farinelli W, Christiani D C, Herrick R F, et al. "Gaseous and particulate content of laser hair removal plume" [Published online Jul. 6, 2016]. JAMA Dermatol. Doi:10.1001/jamadermatol.2016.2097).

In the study, it was found that the plume may contain chemicals that irritate the airways and may be toxic and perhaps even contribute to cancer. Of these chemicals in the plume, about 20 are known as environmental toxins, such as carbon monoxide and 13 are known or suspected to cause cancer, like benzene and toluene. In addition, the bad odor associated with laser hair removal may in addition be harmful and generally detrimental to the total patient experience.

Heretofore, it has been known in the practice of laser hair removal for some physicians to provide a positive ventilation or vacuum evacuation system to remove the smoke and thereby to remove the noxious odors. However, since the patient is present in the room where the treatment is performed during the hair removal process, the patient will still be aware of and may be affected by the odors and the smoke.

Therefore, what is needed is a system and method by which the hair removal plume may be evacuated before it reaches the patient as well as a means to lessen the noxious odors associated with hair removal. It is to this need that the present invention is directed.

SUMMARY OF THE PRESENT INVENTION

In an aspect, an adapter for attachment to a medical application device has an energy generating device and a distal tip for applying the energy generated to skin tissue. The adapter includes a substantially hollow body with a distal end portion and a proximal end portion. The proximal end portion is sized to mount on the distal tip of the energy generating device and the distal end portion is substantially open. The adapter further includes at least one through port extending from the proximal end portion to the open distal end portion of the adapter.

In another aspect, the adapter may further include a conduit operatively connected to the energy generating device, and a source of negative pressure operatively connected to the conduit, wherein the source of negative pressure is activatable; whereby when activated, the source of negative pressure causes a negative pressure at the through port at the open-end portion of the adapter.

In a further aspect, the adapter may further include a filter, the filter being removably mountable on the open distal end portion of the adapter to filter gases when the source of negative pressure is activated. The adapter may further include a second through port extending from the proximal end portion of the adapter.

In yet another aspect, the adapter may include a conduit operatively connected to the energy generating device, and a source of positive pressure operatively connected to the conduit, wherein the source of positive pressure is activatable; whereby when activated, the source of positive pressure causes a positive pressure at the through port at the open-end portion of the adapter.

In an additional aspect, the adapter may further include a source of skin treatment gel. The positive pressure source, when activated, causes the skin treatment gel to be expelled from the distal end portion of the adapter.

In an aspect, the adapter may include a fragrance reservoir operatively attached to the adapter; the source of positive pressure may be operable to selectively disperse a fragrance in the vicinity of the open-end portion of the adapter.

In another aspect, the energy generating device may be one or more of: a laser energy device, an IPL device, a RF device and an ultrasonic device.

In another aspect, a method of reducing smoke plume and debris from the application of energy to skin tissue includes: providing the above adapter; attaching the adapter to the distal tip of the energy generating device; attaching the through port to a source of negative pressure; activating the energy generating source towards the skin tissue; activating the source of negative pressure one or more of: before, during and after activation of the energy source, whereby smoke plume and debris from the skin tissue due to the activation of the energy source is withdrawn from the site through the through port on the adapter by the source of negative pressure.

In a further aspect of the method, the energy generating device may be one or more of: a laser energy device, an IPL energy device, a RF energy device and an ultrasound energy device and may further include a filter. The filter may be removably mountable on the open distal end portion of the adapter to filter gases when the source of negative pressure is activated.

In yet another aspect, the method may further include a second through port extending from the proximal end portion of the adapter and a conduit operatively connected to the energy generating device, and a source of positive pressure operatively connected to the conduit, wherein the source of positive pressure is activatable; the method may further include the step of activating the source of positive pressure, whereby, when activated, the source of positive pressure causes a positive pressure at the through port at the open end portion of the adapter.

In yet a further aspect, the method may further include providing a source of skin treatment gel, and the step of activating the positive pressure source to cause the skin treatment gel to be expelled from the distal end portion of the adapter.

In an additional aspect, the method may further include providing a fragrance reservoir operatively attached to the adapter and activating the source of positive pressure to selectively disperse a fragrance in the vicinity of the open-end portion of the adapter.

DETAILED DESCRIPTION OF THE PRESENT INVENTION

Figure 1:
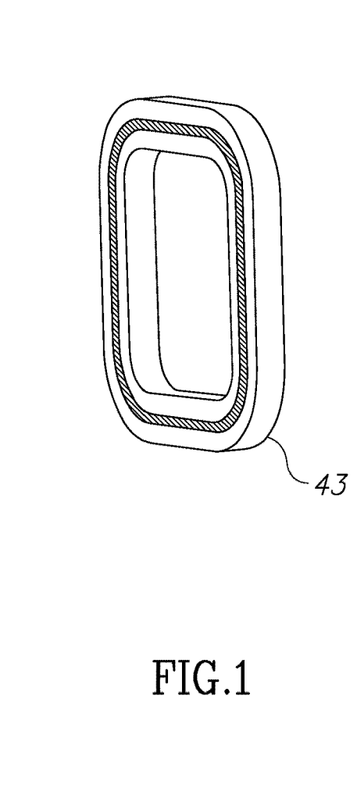
FIG. 1 illustrates the adapter of the present invention mounted on an application device handpiece.

The present invention is directed to an adapter which may be fitted upon and connected to a laser handpiece. FIG. 1 illustrates a somewhat typical laser handpiece 10. While the discussion here is directed to a laser handpiece, it is to be understood that the active device may be instead an IPL lamp device, or a RF device or an ultrasound device, all and any of which may be used for hair removal, although the laser and IPL devices are the most commonly used for hair removal that may encounter a smoke plume as discussed above. In addition, the adapter of the present invention may be used in aesthetic applications other than or in addition to hair removal in which odors may be produced by operation of a device on the skin tissue.

Returning to FIG. 1, the device may include an activation trigger 12 that activates a laser device that may either contained in the handpiece 10 or may be remotely located in an associated console that passes the laser pulse to the handpiece through, for example, an optical fiber contained within an umbilical cord or an optical tube with mirrors (as in conventional CO2 laser devices). An umbilical 14 may terminate at the handpiece and be connected to the console. The umbilical cord may contain the optical fiber, electrical power for the handpiece, cooling tubes or conduits to cool the tip of the handpiece, etc.

In addition, the umbilical cord may include conduits or tubes that connect the handpiece to sources of external negative pressure 11 and positive external pressure 15, the purposes of which are detailed below. It is also envisioned that these conduits or tubes may be directly connected to an adapter 16 and not go through the handpiece itself.

Figure 2:
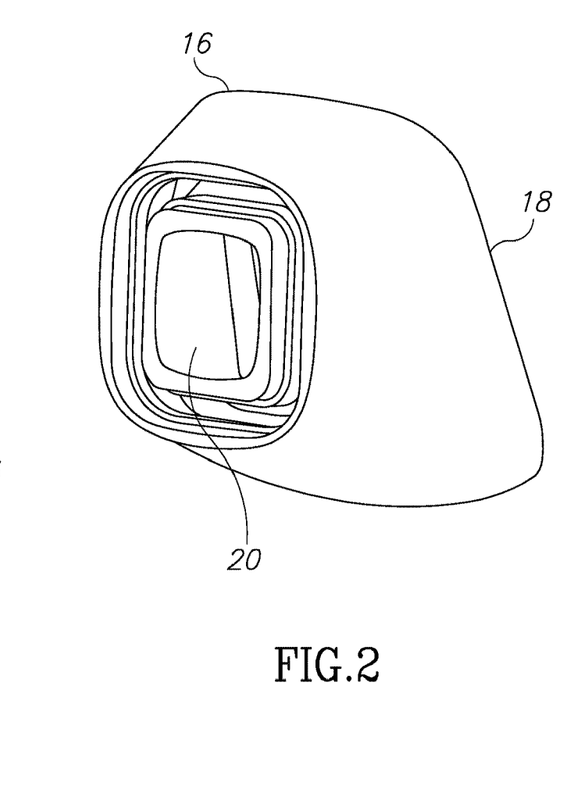
FIG. 2 illustrates the adapter of the present invention.
Figure 3:
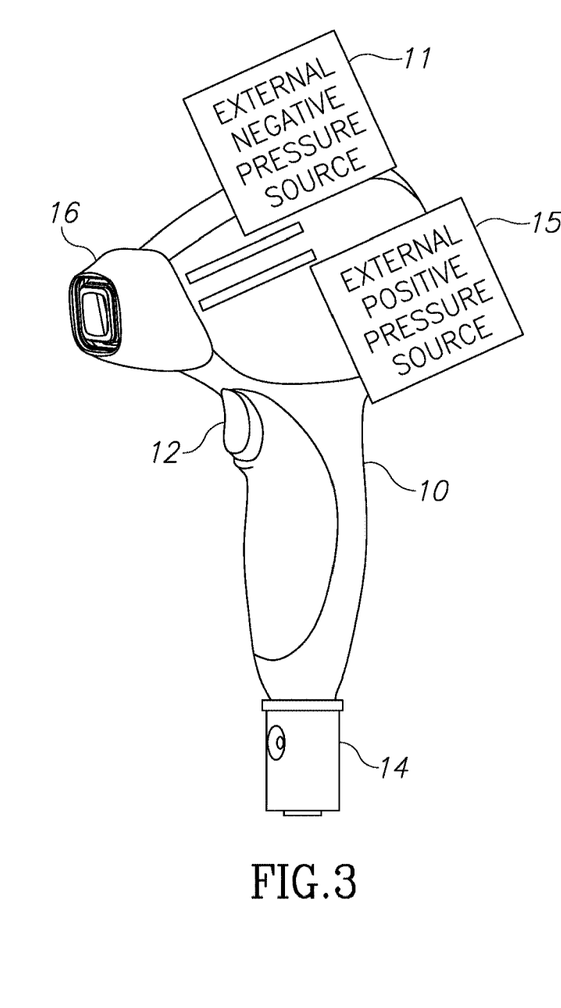
FIG. 3 illustrates a filter device used with the adapter of FIG. 2.

The adapter 16 may be mounted on and/or over the tip of the handpiece as shown in FIG. 3 and shown unattached in FIG. 2. The adapter may be made of a material that is disposable so that a new and clean adapter may be used for each new patient. The adapter has an open back or proximal end 18 that is fit onto the tip of the handpiece 10, by a simple friction fit or by clips or other known simple devices to connect two devices. The adapter is substantially hollow inside its interior and has an opening 20 at its distal end. Optionally, the opening 20 may be sized to receive a filter 43 as shown in FIG. 1.

The filter 43 may be mounted within the opening 20 of the adapter or in a close vicinity around it in a dedicated slot like the slot 48 shown in FIG. 4A, discussed below. While shown in FIG. 3 as substantially rectangular, the filter and for that matter the adapter and its opening may be of any suitable shape and size. The opening 20 in the adapter allows a laser beam from a laser source to travel through the handpiece, into the proximal end of the adapter and through the opening 20 to impinge on skin tissue to be treated. The adapter may contact the skin tissue or be placed a distance from the skin tissue, as is conventionally known. The adapter may be made of a soft material if it is to contact the skin tissue. In addition, the adapter 16 may be sized to have an opening 20 that is large enough to accommodate a laser handpiece tip or an IPL handpiece tip made of glass or another material that may contact the skin tissue as is conventionally known. The adapter 16, as mentioned, may be structured to include a dedicated slot 48 around the periphery of the opening 20 which is configured to accept the filter 43 which in turn may include a filter material 45 with a chosen fragrance. An air gap may be maintained between the filter and skin to allow for proper suctioning of the smoke plume from the treatment site.

Figure 4A:
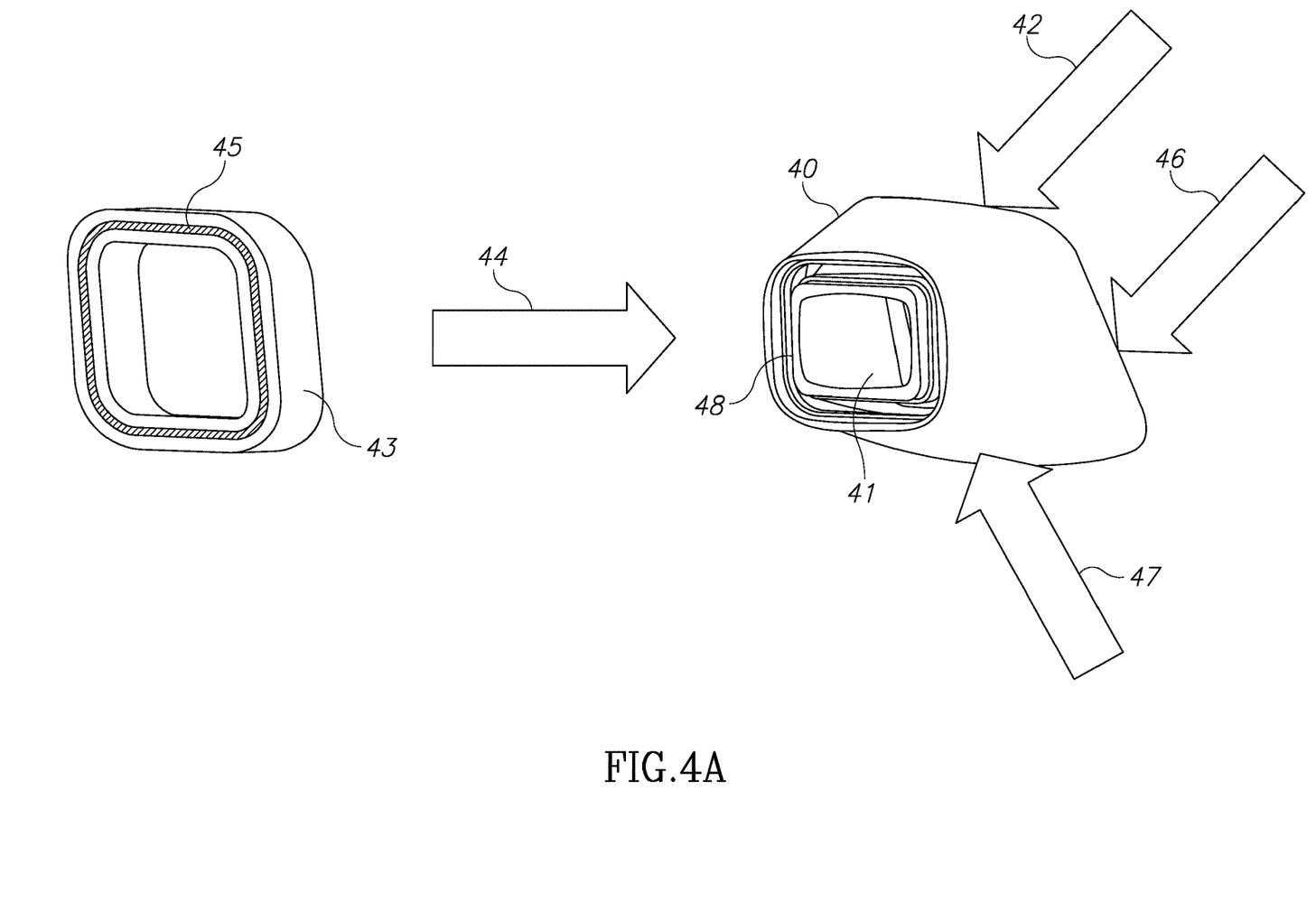
FIGS. 4A and 4B illustrate the adapter of the present invention with input ports.

Turning now to FIG. 4A, that figure shows the adapter 40 with a negative pressure port 42, a positive pressure port 47 and a gel dispensing port 46, to be explained presently. In operation, upon activation of the laser source, the laser energy may cause the exposed hair follicles to be burnt and vaporized, thus producing the smoke plume discussed above. With the present invention, the negative pressure port may be activated either before, during or after (or at all three times) activation of the laser source so that any smoke plume or other debris is sucked up into the opening 41 if open or into the periphery around the opening 41 containing the filter material 45 if, for example, the opening 41 is occupied by a laser or IPL tip. In this manner, the smoke plume and other debris are sucked up and sent along conduits or tubes to outside the vicinity of the patient treatment site.

In FIG. 4A, a filter 43 may be mounted in or on the distal end of the adapter 40 by mounting it in a direction 44. The filter 43 and more specifically the filter material 45 in the filter 43 may be designed to protect the negative pressure conduit present in the adapter from clogging up. A clogged filter may easily be replaced by physician either after the treatment or may even be replaced a number of times during the treatment.

Figure 4B:
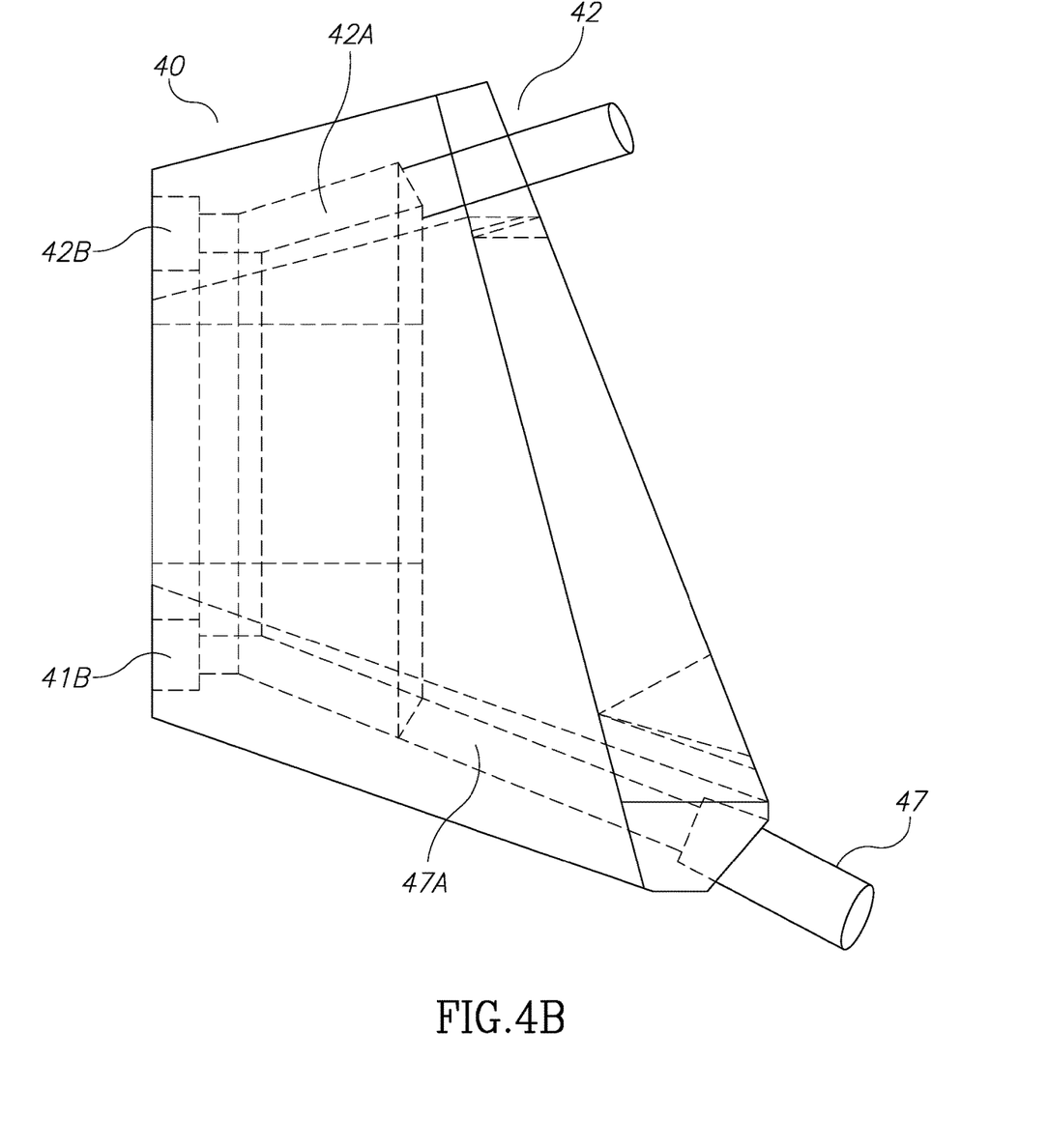

Turning now to FIG. 4B, that figure is similar to the adapter 40 in FIG. 4A but shows the passages within the adapter that carry positive pressure and negative pressure through the adapter to the distal portion of the adapter. Thus, the positive pressure port 47 is connected to a passage 47A that goes from the proximal portion of the adapter 40 to the distal portion of the adapter at 47B. Similarly, FIG. 4B shows the passage of the negative pressure port 42 from the proximal portion of the adapter through passage 42A to 42B at the distal portion of the adapter.

In addition, the adapter may contain or be connected to a gel reservoir which is configured to hold within an amount of optical or thermal coupling material. Such materials are well known in the in the art and are usually spread on the skin tissue prior to the activation of the laser or the IPL device. Here, with the gel reservoir contained either in the adapter or in a separate container connected to the adapter, the positive pressure input port 46 may be activated in a known manner to push the gel from the gel dispenser out of the distal end of the adapter 40 and onto the skin surface skin tissue surface.

As mentioned, in addition to smoke plume and other debris, the vaporizing hair during laser treatment may also cause noxious odors to emanate from the treatment site. While some of the odors may be evacuated through the negative pressure port 42, a fragrance reservoir may be incorporated into either the handpiece or in the adapter which may release a fragrance material into the treatment area during the activation of the laser energy on the IPL. Also, the fragrance reservoir may be a separate container connected to the adapter and/or the handpiece. The fragrance may be dispersed into the area of the adapter either using positive pressure or negative pressure from the respective positive pressure input port or the negative pressure port.

The filter 43 discussed above may itself contain a fragrance that is released during the activation of the vacuum, laser or the IPL energy. The fragrance reservoir may contain multiple, different fragrances that may be offered to a patient to choose from based on his or her personal preferences. Thus, the filter 43 may act both to filter out some of the elements in the smoke plume or debris coming from the treatment site as well as a reservoir to contain a fragrance to be released upon activation of the laser device or the IPL energy.

From the foregoing, it is seen that an adapter may or may not include a gel dispenser, may not include a fragrance reservoir, and they may not include a filter, or an adapter may be constructed to include all of the above, that is, a gel dispenser, a filter and a fragrance reservoir. If this were to be the case, and operator of the device may first dispense gel onto the skin tissue using the positive pressure from the positive pressure input port to push the gel onto the skin tissue. After that step, the operator may turn on the negative pressure through the negative pressure input port prior to activating the laser or IPL energy device so that, when activated, any debris or smoke plume would be sucked up into the adapter and outside the treatment area. At the same time, positive pressure from the positive pressure input port, may be utilized to introduce a fragrance into the area of skin treatment.

Figure 5A:
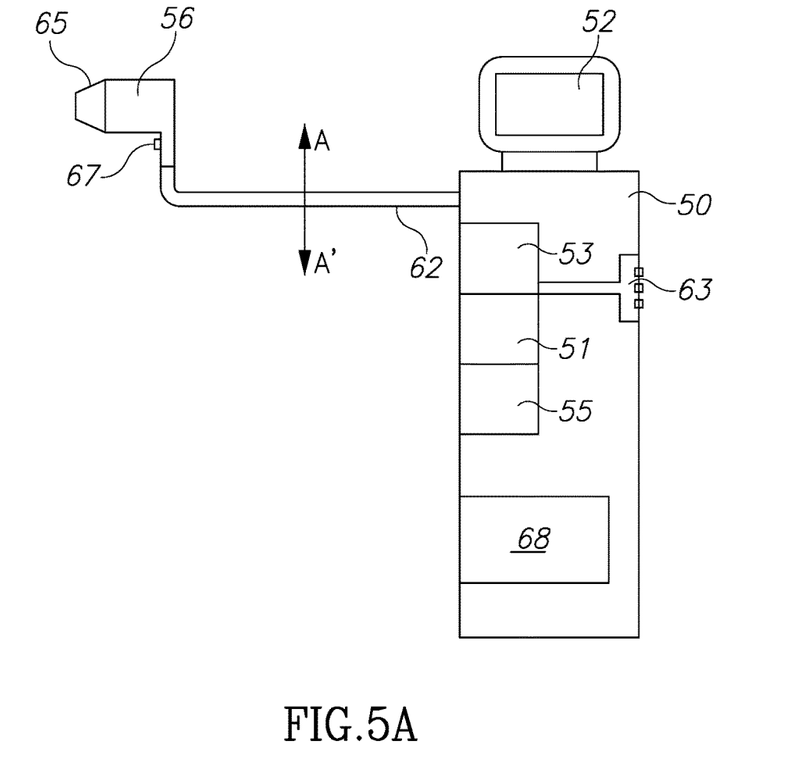
FIGS. 5A and 5B illustrate the structure of the adapter in relation to the system to which it is attached.
Figure 5B:
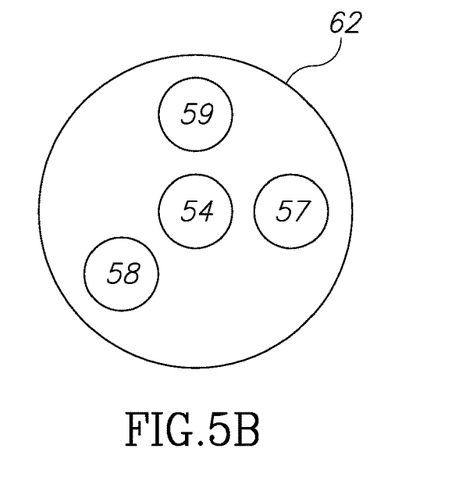
Figure 6A:
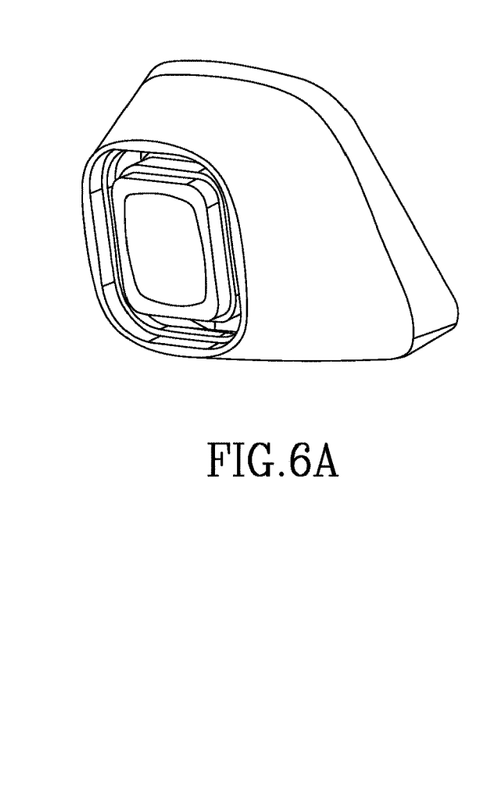
FIGS. 6A through 6M illustrate the adapter of the present invention in various views.
Figure 6B:
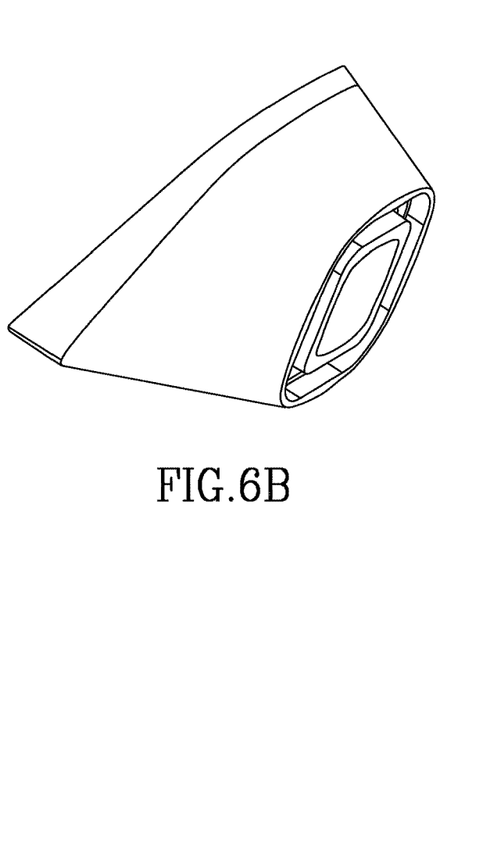
Figure 6C:
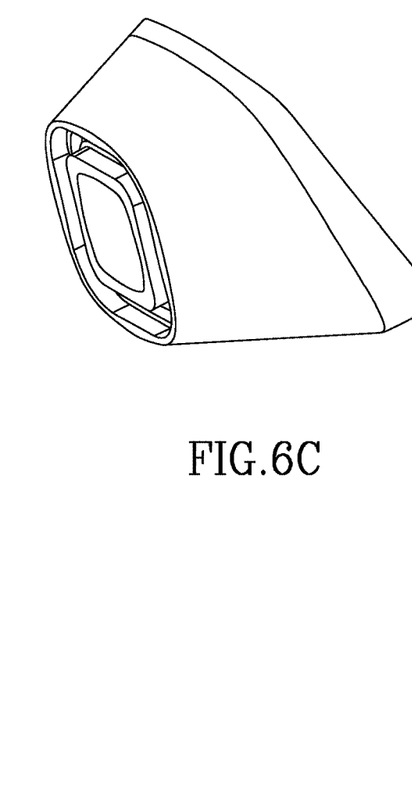
Figure 6D:
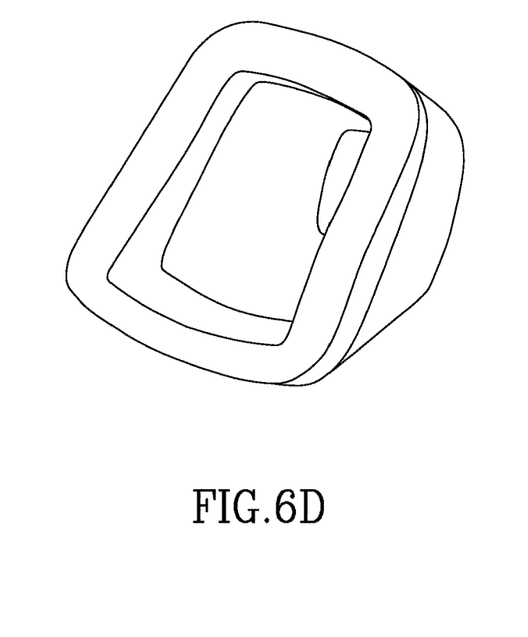
Figure 6E:
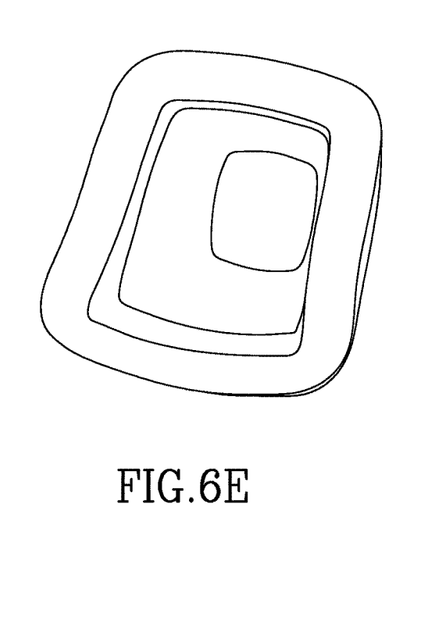
Figure 6F:
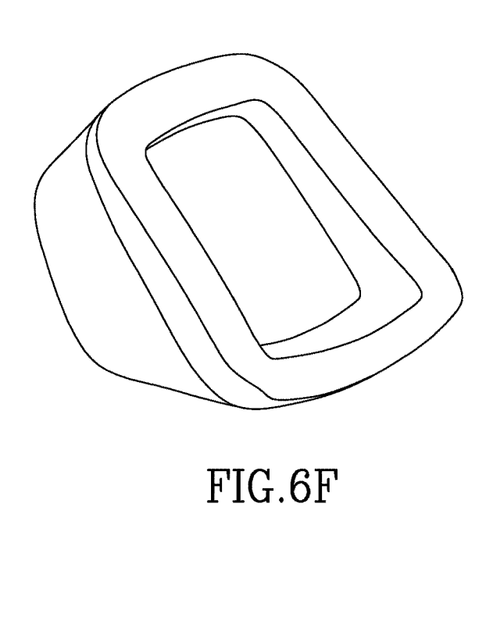
Figure 6G:
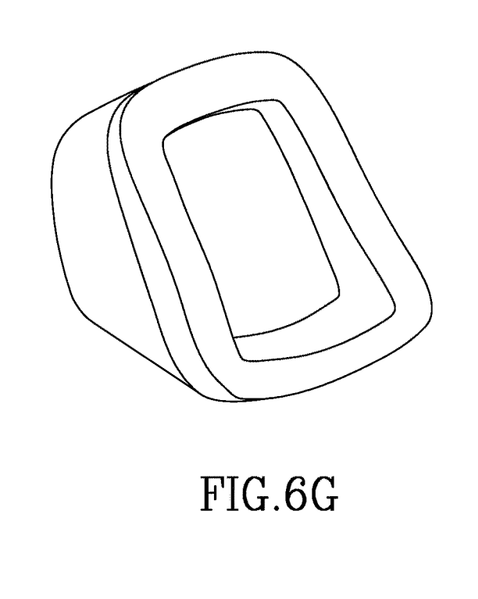
Figure 6H:
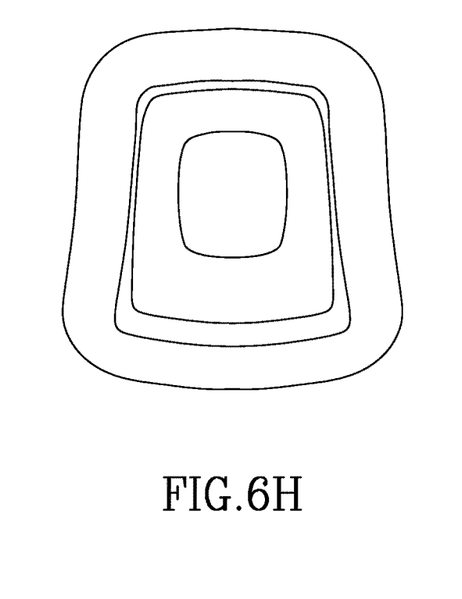
Figure 6I:
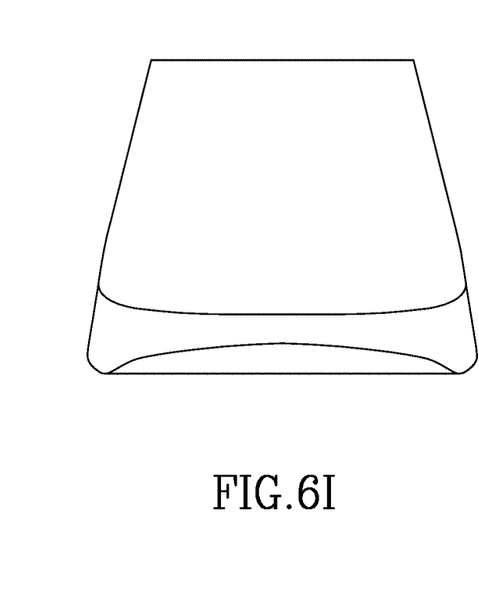
Figure 6J:
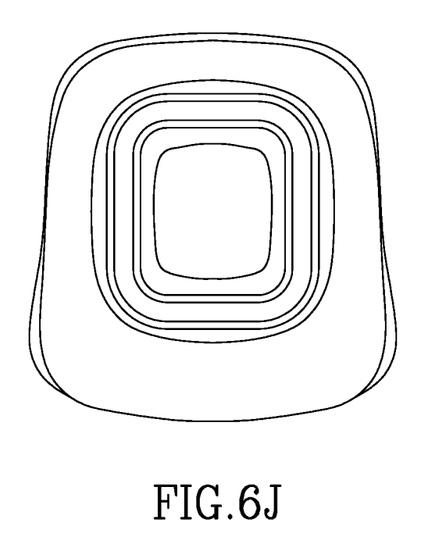
Figure 6K:
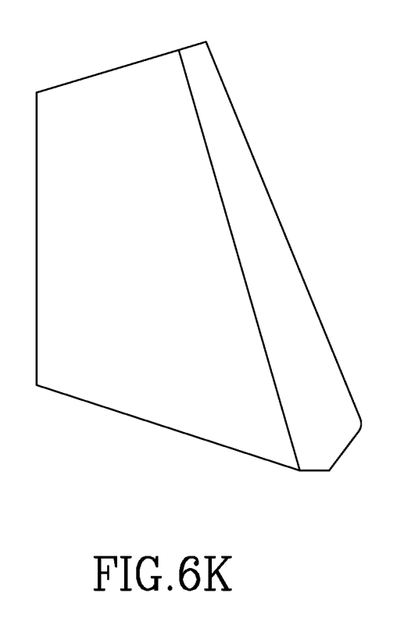
Figure 6L:
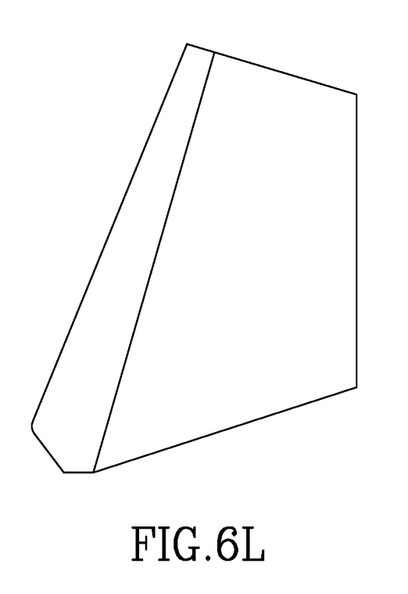
Figure 6M:
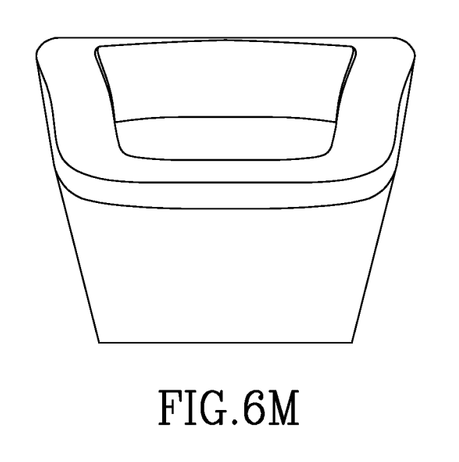

Turning now to FIGS. 5A and 5B, these figures include a console or base unit 50. The base unit 50 includes a GUI screen 52 known in the art through which the operation of the energy generating device may be controlled. The base unit may also include a programmable controller. The programmable controller acts through suitable processing hardware and software to implement the operation of the energy generating device and the adapter. The console may also include an umbilical cord 62 of a known construction. The device handpiece 56 (like that shown as 10 in FIG. 1) and an adapter 6465? (like that shown as 16 in FIG. 1) are attached to the distal portion of the umbilical 62. The console may include a source for generating a negative pressure (vacuum) 53, a source of positive pressure 51, and a source of gel 55. Each of these sources may be operatively connected to the energy device 56 through the umbilical 62. As shown in FIG. 5B, a conduit 54 may contain electrical and other connections (including cooling conduits) connecting the device 56 to the console 50. The conduits 57, 58 and 59 may be conduits for connection of the sources of negative pressure (which may be a vacuum pump), positive pressure and gel supply to and through the device 56 and its attached adapter 65. A trigger or other control 67 may selectively activate the energy generating source 68 within the console or within the handpiece and the sources of negative pressure, positive pressure and gel dispensing. A further conduit 63 may receive the smoke plume and other debris through the action of the negative pressure source 53 and dispose of the evacuant for filtering or other disposal.

What is claimed is:

1. An adapter for attachment to a medical application device having an energy generating device and a distal tip for applying the energy generated to skin tissue, comprising:
   a substantially hollow body having a distal end portion and a proximal end portion;
   the proximal end portion sized to mount on the distal tip of the energy generating device;
   the distal end portion having a central open portion surrounded by a slot around the open portion;
   the adapter further comprising at least one through port extending from the proximal end portion to the central open portion of the open distal end portion of the adapter;
   further comprising a conduit operatively connected to the energy generating device, and a source of negative pressure operatively connected to the conduit, wherein the source of negative pressure is activatable; whereby when activated, the source of negative pressure causes a negative pressure at the slot around the central open portion of the open distal end portion of the adapter; and
   further comprising a filter, the filter being removably mountable within the slot to filter gases when the source of negative pressure is activated, the filter being recessed in the slot so as to maintain an air gap between the filter and the skin tissue to facilitate removal of smoke plume through the through port.

2. The adapter of claim 1, further comprising a second through port extending from the proximal end portion of the adapter.

3. The adapter of claim 2, further comprising a conduit operatively connected to the energy generating device, and a source of positive pressure operatively connected to the conduit, wherein the source of positive pressure is activatable; whereby when activated, the source of positive pressure causes a positive pressure at the through port at the open-end portion of the adapter.

4. The adapter of claim 3, further comprising a source of skin treatment gel, and wherein the positive pressure source when activated causes the skin treatment gel to be expelled from the distal end portion of the adapter.

5. The adapter of claim 3, further comprising a fragrance reservoir operatively attached to the adapter, the source of positive pressure operable to selectively disperse a fragrance in the vicinity of the open-end portion of the adapter.

6. The adapter of claim 1, wherein the energy generating device is one or more of: a laser energy device, an IPL device, a RF device and an ultrasonic device.

7. A method of reducing smoke plume and debris from the application of energy to skin tissue comprising:
   providing the adapter of claim 1;
   attaching the adapter to the distal tip of the energy generating device;
   attaching the through port to a source of negative pressure;
   activating the energy generating source towards the skin tissue;
   activating the source of negative pressure one or more of: before, during and after activation of the energy source;
   whereby smoke plume and debris from the skin tissue due to the activation of the energy source is withdrawn from the site through the filter, then through the through port on the adapter by the source of negative pressure.

8. The method of claim 7, wherein the energy generating device is one or more of: a laser energy device, an IPL energy device, a RF energy device and an ultrasound energy device.

9. The method of claim 7, further comprising a second through port extending from the proximal end portion of the adapter.

10. The method of claim 7, further comprising providing a source of skin treatment gel, the method further comprising the step of activating the positive pressure source to cause the skin treatment gel to be expelled from the distal end portion of the adapter.

11. The method of claim 7, further comprising providing a fragrance reservoir operatively attached to the adapter and activating the source of positive pressure to selectively disperse a fragrance in the vicinity of the open-end portion of the adapter.

\* \* \* \* \*